(12) United States Patent
Coffee

(10) Patent No.: US 6,880,554 B1
(45) Date of Patent: *Apr. 19, 2005

(54) DISPENSING DEVICE

(75) Inventor: Ronald Alan Coffee, Haslemere (GB)

(73) Assignee: Battelle Memorial Institute, Columbus, OH (US)

( * ) Notice: Subject to any disclaimer, the term of this patent is extended or adjusted under 35 U.S.C. 154(b) by 381 days.

This patent is subject to a terminal disclaimer.

(21) Appl. No.: 09/642,982

(22) Filed: Aug. 21, 2000

Related U.S. Application Data

(63) Continuation of application No. 08/492,204, filed on Jun. 2, 1995, now Pat. No. 6,105,571, which is a continuation of application No. PCT/GB93/02634, filed on Dec. 22, 1993.

(30) Foreign Application Priority Data

Dec. 22, 1992 (GB) .............................................. 9226717

(51) Int. Cl.[7] ............................................ A61M 11/00
(52) U.S. Cl. ............................ 128/200.14; 128/203.12; 128/203.27
(58) Field of Search ....................... 128/203.15, 203.27, 128/202.25, 200.14, 203.12; 239/505, 507, 513, 514, 343, 366

(56) References Cited

U.S. PATENT DOCUMENTS

| | | |
|---|---|---|
| 2,723,646 A | 11/1955 | Ransburg |
| 2,945,443 A | 7/1960 | Aver et al. |
| 3,096,762 A | 7/1963 | Winchell |
| 3,131,131 A | 4/1964 | Wehner |
| 3,232,292 A | 2/1966 | Schaefer |
| 3,456,646 A | 7/1969 | Phillips et al. |
| 3,811,620 A * | 5/1974 | Gebhardt .................... 239/499 |
| 3,837,573 A | 9/1974 | Wagner |
| 3,897,905 A | 8/1975 | Tadewald |

(Continued)

FOREIGN PATENT DOCUMENTS

| | | |
|---|---|---|
| DE | P 2008769 | 9/1970 |
| DE | 4106564 A1 | 9/1992 |
| EP | 0029301 A1 | 5/1981 |
| EP | 0029301 | 12/1984 |

(Continued)

OTHER PUBLICATIONS

Article entitled: *Charging Liquid Spray by Electrostatic Induction* authored by: S. E. Law and H. D. Bowen: taken from Transactions of the ASAE: pp. 501–506; dated 1966.

Primary Examiner—Weilun Lo
Assistant Examiner—Michael G. Mendoza
(74) Attorney, Agent, or Firm—Frost Brown Todd LLC

(57) ABSTRACT

An inhaler, comprising an electrohydrodynamic comminution means, a means for partially or fully discharging the liquid comminution and a conduit through which the liquid comminution is administered, wherein the discharging means is arranged to be activated by inhalation of the user.

8 Claims, 4 Drawing Sheets

U.S. PATENT DOCUMENTS

| | | | |
|---|---|---|---|
| 3,930,061 A | | 12/1975 | Scharfenberger |
| 3,958,959 A | | 5/1976 | Cohen et al. |
| 4,043,331 A | | 8/1977 | Martin et al. |
| 4,044,404 A | | 8/1977 | Martin et al. |
| 4,073,002 A | | 2/1978 | Sickles et al. |
| 4,150,644 A | | 4/1979 | Masaki et al. |
| 4,186,886 A | | 2/1980 | Sickles |
| 4,198,781 A | | 4/1980 | Dykes |
| 4,203,398 A | | 5/1980 | Maruoka |
| 4,216,915 A | * | 8/1980 | Hengartner et al. ........ 239/505 |
| 4,264,641 A | * | 4/1981 | Mahoney et al. ........... 427/483 |
| 4,266,721 A | | 5/1981 | Sickles |
| 4,356,528 A | | 10/1982 | Coffee |
| 4,380,786 A | | 4/1983 | Kelly |
| 4,439,980 A | | 4/1984 | Biblarz et al. |
| 4,467,961 A | | 8/1984 | Coffee et al. |
| 4,476,515 A | | 10/1984 | Coffee |
| 4,508,265 A | | 4/1985 | Jido |
| 4,509,694 A | | 4/1985 | Inculet et al. |
| 4,549,243 A | | 10/1985 | Owen et al. |
| 4,659,012 A | | 4/1987 | Coffee |
| 4,671,269 A | | 6/1987 | Wilp |
| 4,702,415 A | * | 10/1987 | Hughes ................. 128/200.18 |
| 4,703,891 A | | 11/1987 | Jackson et al. |
| 4,735,364 A | | 4/1988 | Marchant |
| 4,748,043 A | | 5/1988 | Seaver et al. |
| 4,749,125 A | | 6/1988 | Escallon et al. |
| 4,776,515 A | | 10/1988 | Michalchik |
| 4,788,016 A | | 11/1988 | Colclough et al. |
| 4,795,330 A | * | 1/1989 | Noakes et al. ................. 239/3 |
| 4,801,086 A | | 1/1989 | Noakes |
| 4,811,898 A | * | 3/1989 | Murphy ....................... 239/11 |
| 4,829,996 A | * | 5/1989 | Noakes et al. ......... 128/200.14 |
| 4,830,872 A | | 5/1989 | Grenfell |
| 4,846,407 A | | 7/1989 | Coffee et al. |
| 4,962,885 A | | 10/1990 | Coffee |
| 4,979,680 A | | 12/1990 | Bauch et al. |
| 5,044,564 A | | 9/1991 | Sickles |
| 5,086,972 A | | 2/1992 | Chang et al. |
| 5,115,971 A | | 5/1992 | Greenspan et al. |
| 5,180,288 A | | 1/1993 | Richter et al. |
| 5,196,171 A | * | 3/1993 | Peltier ......................... 239/34 |
| 5,222,663 A | | 6/1993 | Noakes et al. |
| 5,267,555 A | * | 12/1993 | Pajalich ................. 128/200.14 |
| 5,341,801 A | * | 8/1994 | Zechner ................. 128/203.15 |
| 5,381,789 A | | 1/1995 | Marquardt |
| 5,382,410 A | * | 1/1995 | Peltier ......................... 239/34 |
| 5,396,882 A | * | 3/1995 | Zapol .................... 128/200.14 |
| 5,402,945 A | | 4/1995 | Swanson |
| 5,409,162 A | | 4/1995 | Sickles |
| 5,483,953 A | | 1/1996 | Cooper |
| 5,511,726 A | | 4/1996 | Greenspan et al. |
| 5,655,517 A | | 8/1997 | Coffee |
| 5,927,618 A | * | 7/1999 | Jefferies et al. .......... 239/690.1 |
| 6,079,634 A | | 6/2000 | Noakes et al. |
| 6,386,195 B1 | * | 5/2002 | Coffee ................... 128/200.14 |
| 6,394,086 B1 | * | 5/2002 | Barnes et al. .......... 128/203.15 |
| 6,457,470 B1 | * | 10/2002 | Coffee ................... 128/200.14 |

FOREIGN PATENT DOCUMENTS

| | | |
|---|---|---|
| EP | 0 102 713 B1 | 9/1987 |
| EP | 0234842 | 9/1987 |
| EP | 0250164 A3 | 12/1987 |
| EP | 0523963 A1 | 7/1992 |
| EP | 0523962 A1 | 1/1993 |
| EP | 523964 A1 | 1/1993 |
| GB | 1297993 | 11/1972 |
| GB | 2018627 A | 10/1979 |
| GB | 2018627 B | 10/1979 |
| GB | 1569707 | 6/1980 |
| GB | 2018627 B | 4/1982 |
| GB | 2 128 900 A | 5/1984 |
| GB | 2 201 873 A | 9/1988 |
| NZ | 195704 | 12/1980 |
| NZ | 198774 | 10/1981 |
| NZ | 191545 | 11/1983 |
| NZ | 191545 | 6/1984 |
| NZ | 195704 | 9/1984 |
| NZ | 198774 | 12/1984 |
| SU | 1005939 A | 6/1981 |
| WO | WO 91/07232 | 5/1991 |
| WO | WO 92/15339 | 9/1992 |
| WO | WO 93/06937 | 4/1993 |

* cited by examiner

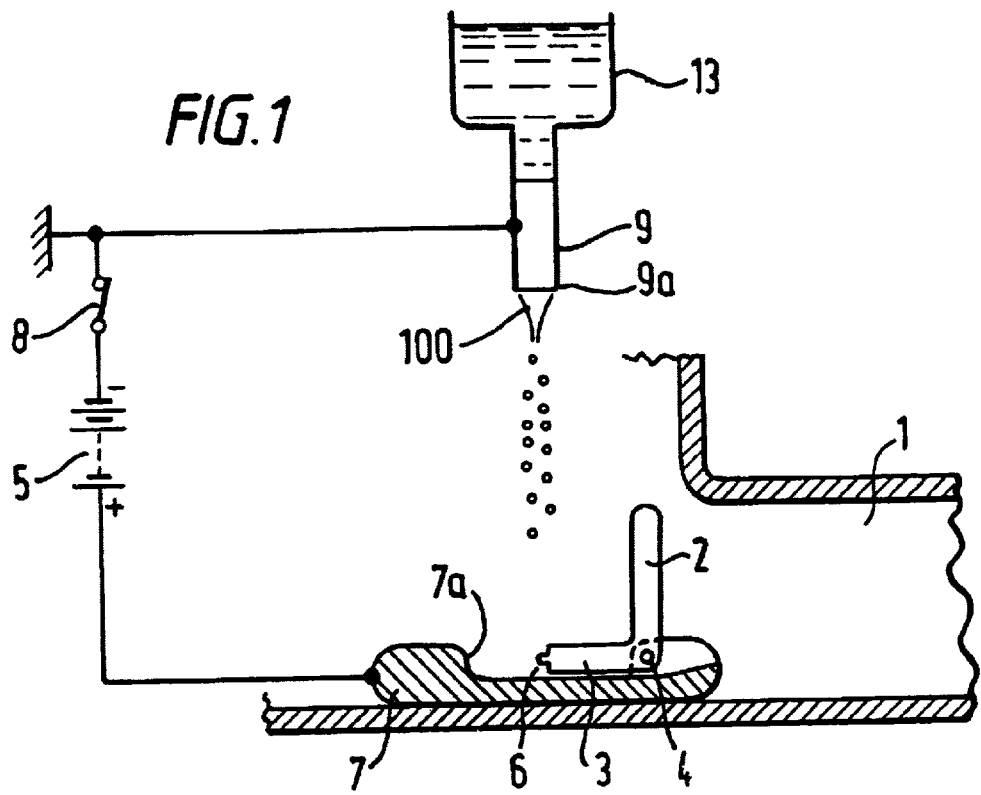
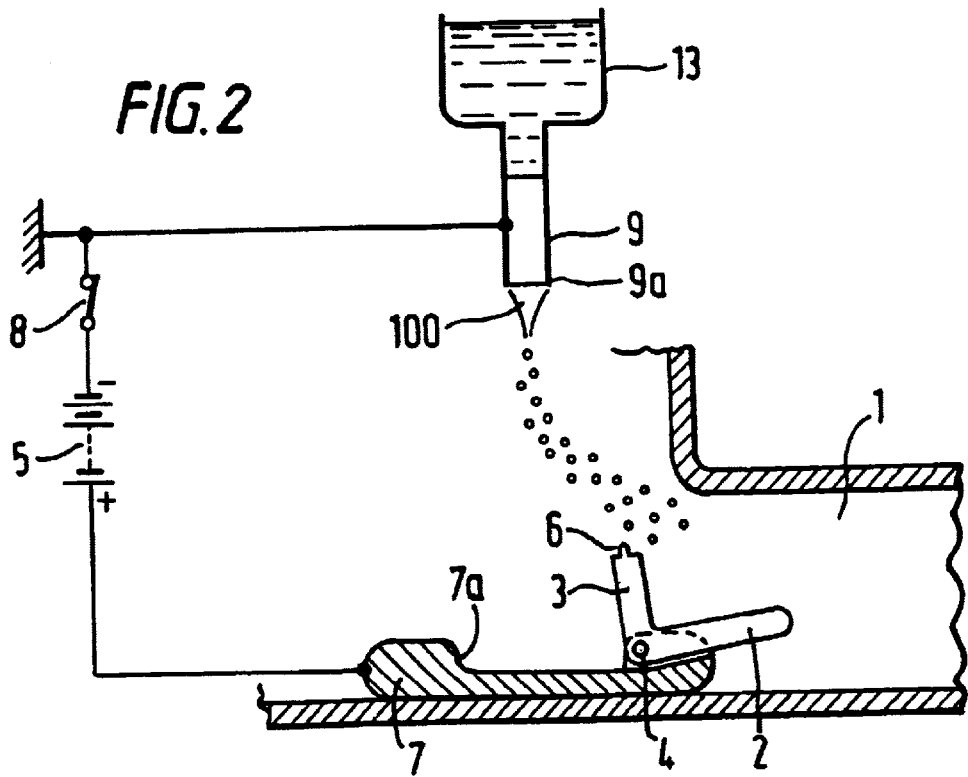

US 6,880,554 B1

DISPENSING DEVICE

This is a Continuation of U.S. Ser. No. 08/492,204 filed Jun. 2, 1995, now Pat. No. 6,105,571 which is in turn a continuation of Ser. No. PCT/GB93/02634 filed Dec. 22, 1993.

The invention relates to a dispensing device for comminuting a liquid and the uses of such a device, especially in medicine.

Dispensing devices are known which produce a finely divided spray of liquid droplets by electrostatic (more properly referred to as 'eletrohydrodynamic') means. The droplet spray in such devices is generated by the application of an electric field to a liquid at a spray head or spray edge. The potential of the applied electric field is sufficiently high to provide comminution of the liquid from the spray head. The droplets produced are electrically charged and thus are prevented from coagulating by mutual repulsion.

Electrohydrodynamic sprayers have potential uses in many areas, including agriculture and the automotive industry and also for dispensing cosmetics and medicines.

United Kingdom patent number 1569707 describes such an electrohydrodynamic spray device principally for use in crop spraying.

United Kingdom patent number 2018627B discloses an electrohydrodynamic spray device wherein the charged droplet spray is fully or partially electrically discharged by means of an earthed electrode having a sharp or pointed edge and located downstream of the spray head. European Patent number 0234842 also uses this technology and relates to an inhaler in which charged droplet spray is discharged prior to inhalation by means of a sharp or pointed discharge electrode carrying an opposite charge to the droplet spray and located downstream of the spray head. The droplets are discharged to facilitate droplet deposition into the respiratory tract by preventing deposition of charged droplets onto the mouth and throat of the user.

A common feature of all known electrohydrodynamic spray devices is that the electric charge used to generate the spray is applied directly to the spray head. It has now surprisingly been found that the direct application of the field is not essential and that the electrohydrodynamic comminution of a liquid may be accomplished by inducing the required electric charge at the spray head. In addition and advantageously, it has been found that the comminutions produced can be partially or fully discharged prior to use.

This method of induced charging has been found to provide better comminution of liquids having lower electrical resistivity.

Accordingly, it is one aspect of the invention that there is provided an electrohydrodynamic dispensing device for comminuting a liquid, wherein the liquid is comminuted by an induced electrical charge.

The dispensing device normally comprises a comminution site, a means for supplying liquid to the comminution site and a means for inducing an electrical charge at the comminution size sufficient to comminute the liquid.

The comminution site may be any conventional electrohydrodynamic comminution site such as a surface or edge generally provided by a thin capillary tube, a nozzle or a slot defined by two parallel plates.

Appropriate means for supplying liquid to the comminution site include mechanical or electrically powered pumps which are capable of providing the required flow rate of liquid to the comminution site such as a syringe pump or the electrically powered pump described in EP 0029301.

The comminution means of the invention can be used with a large range of flow rates, but generally operates with flow rates in the range of between 0.1 to 500 $\mu$l L per second, such as 0.5 to 5 $\mu$L per second, especially for inhaled administration, or 10 to 200 $\mu$L per second, especially for agricultural use.

The means for inducing the electrical charge at the comminution site may be any conventional source of electrical charge which in use is capable of inducing a charge sufficient to comminute the liquid from the comminution means including a high voltage generator or a piezo-electric generator. The charge required is usually of the order of 1–20 kilovolts for example 10 kilovolts.

After formation of the liquid comminution, the electrically charged liquid droplets are attracted towards and will impact the means for inducing the electrical charge at the comminution site. In a preferred aspect of the present device, there is therefore provided a means for partially or fully electrically neutralising the liquid comminution before it impacts the induced charging means. One suitable means for partially or fully electrically discharging the liquid comminution is a sharp or pointed discharge electrode located downstream of the comminuted liquid.

The sharp or pointed discharge electrode may be earthed or it may be maintained at a polarity opposite to that of the induced charging means by connection to a suitable charging means. In either case the comminuted liquid is partially or fully discharged by a cloud of charged ions produced from the surrounding air having an opposite electrical charge to that on the comminuted liquid spray. The ion cloud is attracted towards, collides with and thereby partially or fully discharges the liquid spray.

In one particularly advantageous form of the device, the means for fully or partially discharging the liquid comminution is provided by a combination of the sharp or pointed discharge electrode and at least one capacitor, the capacitor acting to absorb the charge from the gaseous ions from the sharp or pointed discharge electrode until the induced comminution of the liquid is established, the capacitor is arranged to absorb the ions until it reaches a predetermined potential at which potential it ceases to absorb the ions thereby allowing them to partially or fully discharge the liquid comminution.

Generally, the capacitor is chosen to have a time constant having the same order as the time required to establish the liquid comminution spray cloud. Thus the time constant will have a value, in seconds, which is the product of the capacitance, C and the resistance, R, of the capacitor.

The value of CxR for the capacitor is chosen so that the capacitor will charge until it reaches a prearranged potential sufficient to modify the electric field, the capacitor then discharges towards the established spray cloud. Generally, the time-constant required will be of the order of seconds or a number of milliseconds. For example, a capacitor of 0.1 microfarad with a resistance of 10 megohms will produce a time constant of one second.

In yet a further aspect, the means for fully or partially discharging the liquid comminution is provided by an electrode arranged to have a first surface capable of producing an electric field sufficient to induce the required charge for liquid comminution in the comminution means and also to impart sufficient inertia to the liquid comminution so that it substantially bypasses the first surface, the electrode also having a second surface capable of producing an ionic discharge to fully or partially discharge the liquid comminution.

Generally, the second surface is shaped to have a sharp edge or a point which in use produces the ionic discharge.

Suitably, the electrode is an annular electrode coaxially located with respect to the intended flight path of the liquid comminution, in use, the upper surface of the annular electrode induces the required charge in the comminution means, the lower surface being shaped so as to produce the ionic discharge.

In operation the field pattern of the upper surface of the annular electrode is such that the comminution is directed onto an axial flight path with respect to the annular electrode and is provided with sufficient inertial force to substantially bypass the first surface, the comminution is then fully or partially discharged by the gaseous ions produced by the second surface.

The device of the invention may be used to dispense liquids comprising components useful for human or animal health care, such as medicaments for pharmaceutical or public health care use or medically useful compounds such as anesthetics.

Suitable liquids include liquids comprising components for agricultural use such as pesticides or biocides.

Suitable liquids include liquid cosmetic formulations.

Other suitable liquids include paints and inks. Also included are liquids for providing aromas.

Preferred liquids are pharmaceutically active liquids.

The communition means of the dispenser provides liquid droplets within the range of from about 0.1 to about 500 microns in diameter. More usually from 0.1 to 200 microns, such as 1.0 to 200 microns: Examples include droplets within the range of 5.0 to 100, 0.1 to 25, 0.5 to 10 or 10 to 20 microns. A favoured range for inhaled administration is 0.1 to 25 or 0.5 to 10 microns, especially for administration to the lower respiratory tract, and 10 to 25 microns, especially for administration to the upper respiratory tract.

For a given liquid the diameter of the droplets can be controlled by varying the applied voltage and liquid flow rate using routine experimental procedures.

Liquids having viscosities within the range of from 1 to 500 centipoise and resistivities in the range of from $10^2$–$10^8$ ohm m can be comminuted by the present device.

As stated this method of induced charging has been found to provide better comminution of liquid having a lower electrical resistivity, such as is the case of aqueous solvents, including solvent mixtures, and solutions thereof and low resistivity organic solvents such as alcohols.

One favoured use of the device of the invention is for the dispensation of a comminuted liquid for inhalation.

Accordingly, in one preferred aspect of the invention there is provided a device for comminuting a liquid for inhalation, wherein the liquid is comminuted by an induced electrical charge.

The device of the invention may be adapted into any embodiment form which dispenses comminuted liquid for inhalation, for both medicinal and non-medicinal use.

Non-medicinal inhalation uses includes dispensing perfumes and aromas.

Preferably, the device is in the form of an inhaler, for the inhaled delivery of a medicament.

A preferred liquid is therefore a liquid medicament formulation adapted for inhaled administration.

Medicaments suitable for adaption for inhaled administration include those used for the treatment of disorders of the respiratory tract, such as reversible airways obstruction and asthma and those used in the treatment and/or prophylaxis of disorders associated with pulmonary hypertension and of disorders associated with right heart failure by inhaled delivery.

One problem associated with inhalers is coordinating the release of the liquid spray with inhalation by the user. It is a further aspect of the present invention that there is provided a means which facilitates this problem.

Accordingly, there is also provided an inhaler, comprising an electrohydrodynamic comminution means, a means for partially or fully discharging the liquid comminution and a conduit through which the liquid comminution is administered, wherein the discharging means is arranged to be activated by inhalation of the user.

Suitably, the electrohydrodynamic comminution means comprises a communition site and a charging means, the charging means acting directly or by induction to produce the required charge on the communition means, favourably acting by induction.

Suitably, the electrohydrodynamic comminution means comprises a means for supplying liquid to the communition means.

One favoured arrangement wherein the discharging means is activated by inhalation of the user comprises a valve means located so as to open and close the conduit, suitably within the conduit, the valve means being opened by inhalation of the user which then activates the discharging means.

A suitable discharging means is provided by one or more capacitors or by a sharp edged or pointed electrode.

When the discharging means is a sharp edged or pointed electrode, the discharging means is preferably operationally attached to the valve means such that when the valve means opens the sharp edged or pointed electrode is thereby exposed to the communited liquid.

A suitable valve means is a flap valve.

In a particular instance the sharp edged or pointed electrode is fixed so as to extend upwards from the plane of the flap valve, the flap valve being pivotally fixed so as to open and close the conduit, such that when the flap valve pivots open the sharp edged or pointed electrode pivots into the flight path of the comminuted liquid.

Thus in a most particular instance the invention provides an inhaler, the inhaler comprising an electrohydrodynamic comminution site, a means for supplying liquid to the comminution site, a means for charging the comminution site, a sharp edged or pointed electrode for partially or fully discharging the liquid comminution and a conduit through which the liquid comminution is administered, the conduit having a valve means activated by inhalation of the user, wherein the valve means comprises a flap shaped to seal the conduit, the flap being pivotally fixed so as to open and close the conduit, the sharp edged or pointed electrode extends upwards from the plane of the flap valve, such that in use the flap valve pivots open and the discharging means pivots into the flight path of the comminuted liquid.

When the devices comprise a sharp edged or pointed electrode, the arrangement suitably provides that the sharp edged or pointed electrode is electrically shielded from the liquid comminution when the valve means is closed. One particular method of achieving this is that the sharp edged or pointed electrode pivots into a recess formed in the charging means when the valve means closes.

When used herein 'a comminution' includes a liquid droplet spray.

When used herein 'medicament' includes proprietary medicines, pharmaceutical medicines and veterinary medicines.

When used herein, unless more specifically defined herein, 'inhaled administration' includes administration to and via the upper respiratory tract, including the nasal mucosa, and the lower respiratory tract.

The description 'sharp edged or pointed' when used herein in relation to operational parts of the device, such as the electrode, also includes electrical equivalents thereof and hence includes shapes such as ridges and the like. The essential requirement is that the operational part of the device has, or a component or feature of the device has, dimensions which will give rise to a sufficiently high electrical field strength so as to exceed the breakdown strength of the air. This tropic is theoretically described in "Depositional Control of Macroscopic Particles by High Strength Electric Field Propulsion" by R A Coffee, in "Transactions of the Institution of Electrical and Electronic Engineers, Industry Applications, USA", Vo. IA-10 pp 511 to 519, July/August 1974. An example is an electrical field strength of approximately 3 million volts per meter.

The liquid medicinal formulations for use in the device of the invention may be formulated according to conventional procedures, such as those disclosed in the U.S. Pharmacopeia, the European Pharamcopoeia, 2nd Edition, Martindale The Extra Pharmacopoeia, 29th Edition, Pharmaceutical Press and the Veterinary Pharmacopoeia.

The liquid cosmetic formulations for use in the device of the invention may be formulated according to conventional procedures, such as those disclosed in Harry's Cosmeticology, 9th Edition, 1982, George Goodwin, London.

BRIEF DESCRIPTION OF DRAWINGS

FIGS. 1 and 2 illustrate a device with a hinged flap which effects droplets ionization;

Figure 3:
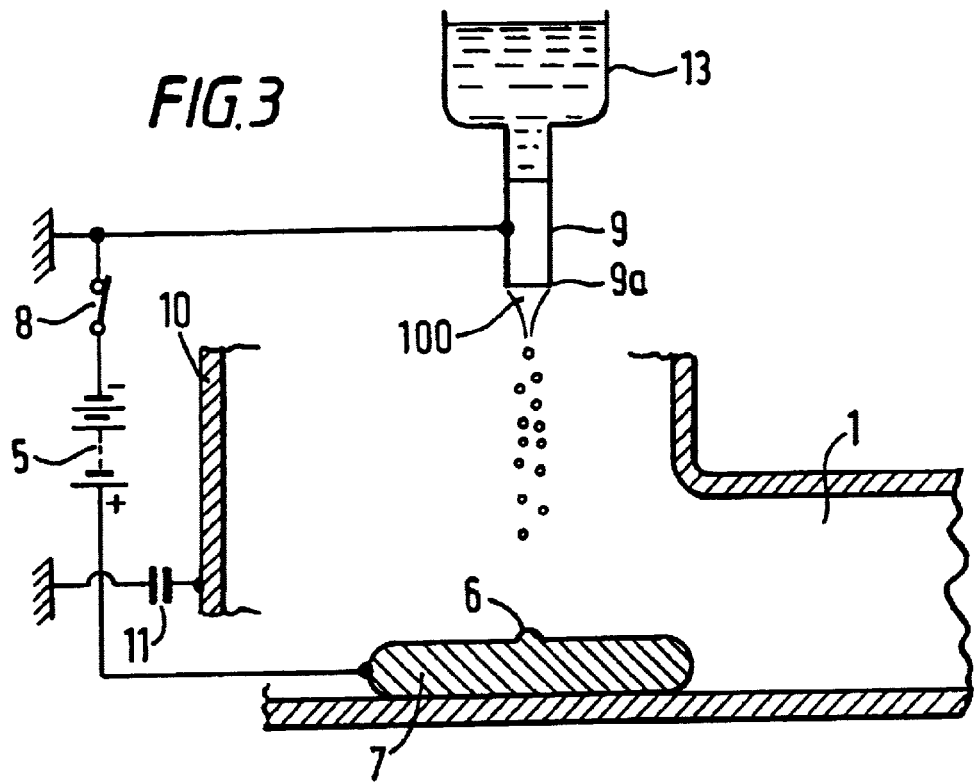
FIG. 3 shows a side view of a device which uses electrically floating conducting surfaces to effect droplet charge.

The invention may now be described, by way of illustration, with reference to the accompanying FIGS. 1 to 5.

In FIGS. 1 and 2, a device of the invention is illustrated in which a pressure reduction created by the action of breathing through a suitable ducting (1) causes a lightweight flap (2), balanced by a second member (3) pivoted at a hinge (4) and connected to a dc high voltage supply of either polarity (5) to revolve through a sufficient degree of arc to allow the second member of the flap to become exposed to the electric field and then create gaseous ions.

The flap value thus has two actions: (a) it opens an air passage (1) to facilitate a flow of droplets; and (b) it simultaneously rotates a balancing member (3) attached to the flap (2) through a sufficient degree of arc to expose a ridge, or nipple (6) having one dimension of less than about 1.0 mm radius of curvature.

The ridge, or nipple (6) may be made of any conducting, or semi-conducting material such as metal, or carbon-loaded plastic, and is connected to a source of high voltage (5). When not actuated by breathing, the ridge will be electrically screened by the surface of a flat electrode (7), also connected to the high voltage source (5). In this position the electrode (7) may be switched on, or off by a simple switch (8).

When switched on, the electrode induces a potential of opposing polarity at the tip of a nearby nozzle (9). This induced potential causes liquid at the tip of the nozzle to emerge as a fast jet which breaks up into charged droplets. The nozzle (9) is connected to earth.

The invention therefor performs more than one function: (a) the flap valve (2) allows droplets to be inhaled only when the valve is actuated by the act of breathing; (b) the principle of induction, rather than direct nozzle charging improves the control of droplet size and maximum flow rate, for those liquids which are difficult to atomize by the electrohydrodynamic process; (c) it overcomes the inevitable consequences of induction charging, which is that the opposite polarity droplets would otherwise be so strongly attracted to the source of the induced voltage (7) that the droplets would not be available for delivery by inhalation, or other forms of deposition onto target surfaces.

In FIG. 3, one or more electrically floating conducting or semi-conducting surfaces (10), attached to one or more capacitors (11) are used to attract and capture the gaseous ions so that the electric field created by the electrode (6) acts directly upon the nozzle (8) without impingement of gas ions. Such gas ions, if allowed to reach the nozzle unimpeded would be expected to modify the electric field surrounding the nozzle so as to prevent the emerging liquid from forming the necessary jet of liquid for atomization by the electrohydrodynamic method. The capacitor(s) is chosen to have a time constant of the same order as the time required to established a spray cloud. This time constant will have a value, in seconds, which is the product of the capacitance, C and the resistance, R, of the capacitor. The value of CxR is thus chosen so that the capacitor will charge by bombardment of gaseous ions, until it reaches a sufficient potential to modify the electric field and to re-direct the ions toward the established spray cloud. Generally, the time-constant required will be of the order of seconds or a number of milliseconds. For example, a capacitor of 0.1 microfarad with a resistance of 10 megohms will produce a time constant of one second. FIG. 3 shows one configuration that will create the required induction potential at the nozzle when the electrode (7) is energized and, after a suitable period, dependent upon the position and time constant of the capacitor(s) will then re-arrange the field to allow gaseous ions to migrate into the spray cloud so as to modify the charges on all droplets to a lower (optimal) or approximately zero value. Such droplets may then be readily inhaled.

The charged droplets are prevented from impinging upon the high voltage electrode (7) by the action of fast moving gaseous ions. These ions are created by the combination of electrode voltage, say one to ten kilovolts dc, and the radius of curvature of the small dimension of the ridge or nipple (6) on the balancing member (3) and by juxtaposition of the nozzle (9), the electrode (7) and the capacitor(s) (11). The capacitor(s) (11) may be used to increase the degree of control of the shape of the field and the timing of the essential reshaping process.

Liquid is supplied to the nozzle (9) from either a container (13) by gravity feed, or by mechanical pumping, or by one of the electrokinetic pumping device. The liquid is supplied to the nozzle and the induced voltage applied by the electrode (7) before the electric field is modified to create gaseous ions by the actuation of the flap-valve (2) and/or the capacitor(s) (11). Then, at any time after the spray cloud is developed, the breath-actuated valve and/or the capacitor(s) is actuated, whereupon the droplet trajectories are modified; moving away from their direct flight to the electrode (7), through the required angle, say to flow by viscous drag in the air movement caused by normal breathing. This action is virtually instantaneous due to the extremely low inertial forces on droplets used for inhalation therapy, which are generally less than about 10.0 μm in diameter for drug inhalation.

Figure 4:
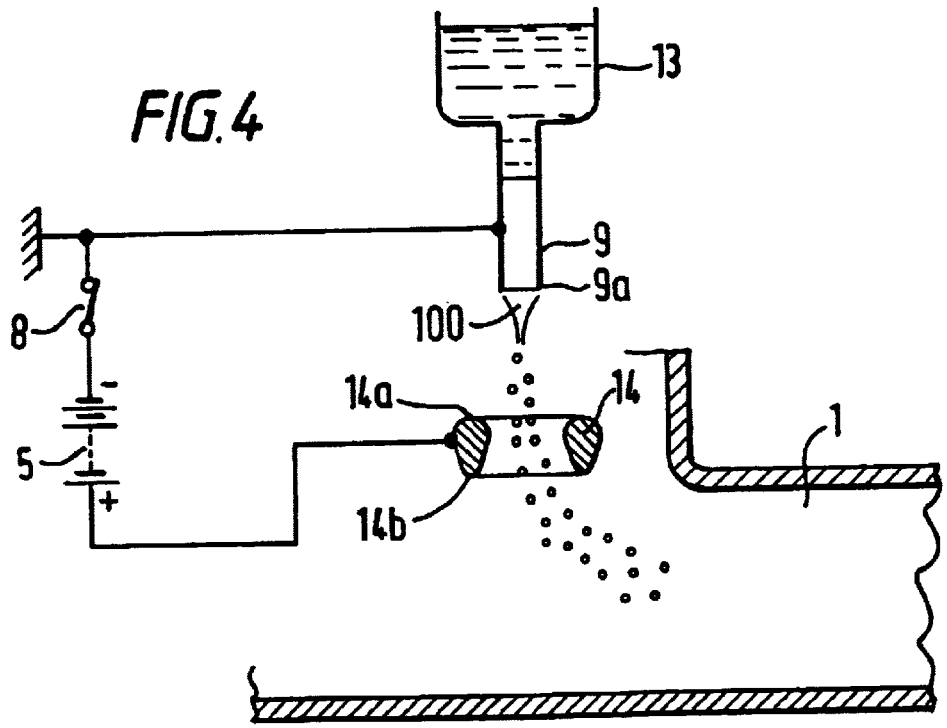
FIG. 4 shows a side view of a device with an induction ring.
Figure 4A:
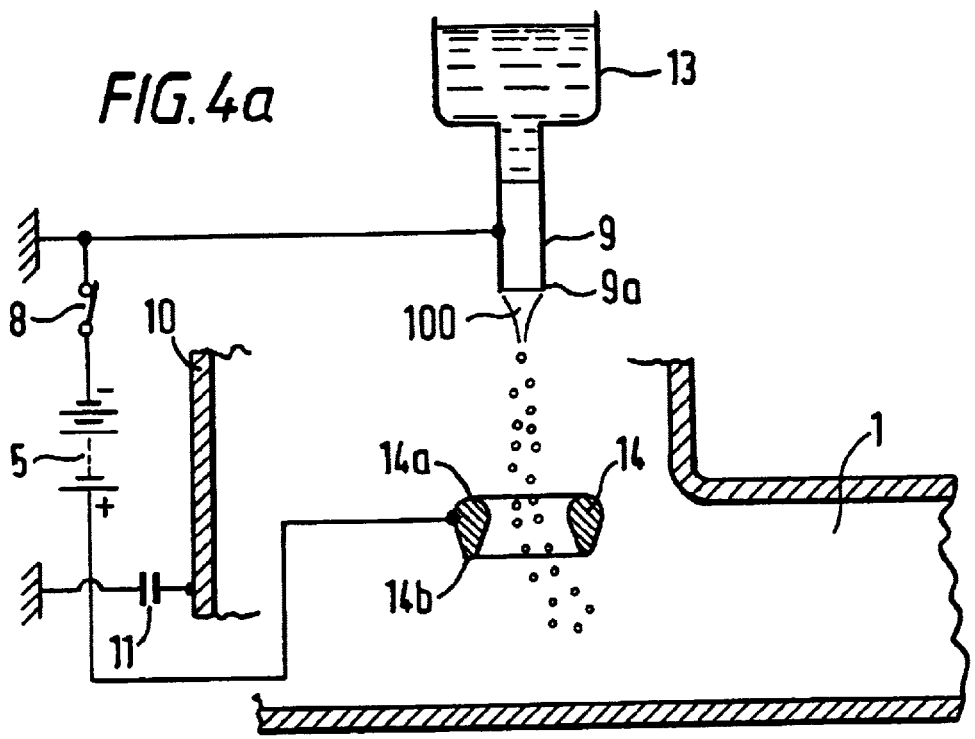
FIGS. 4a and 4b show modifications of the device shown in FIG. 4.
Figure 4B:
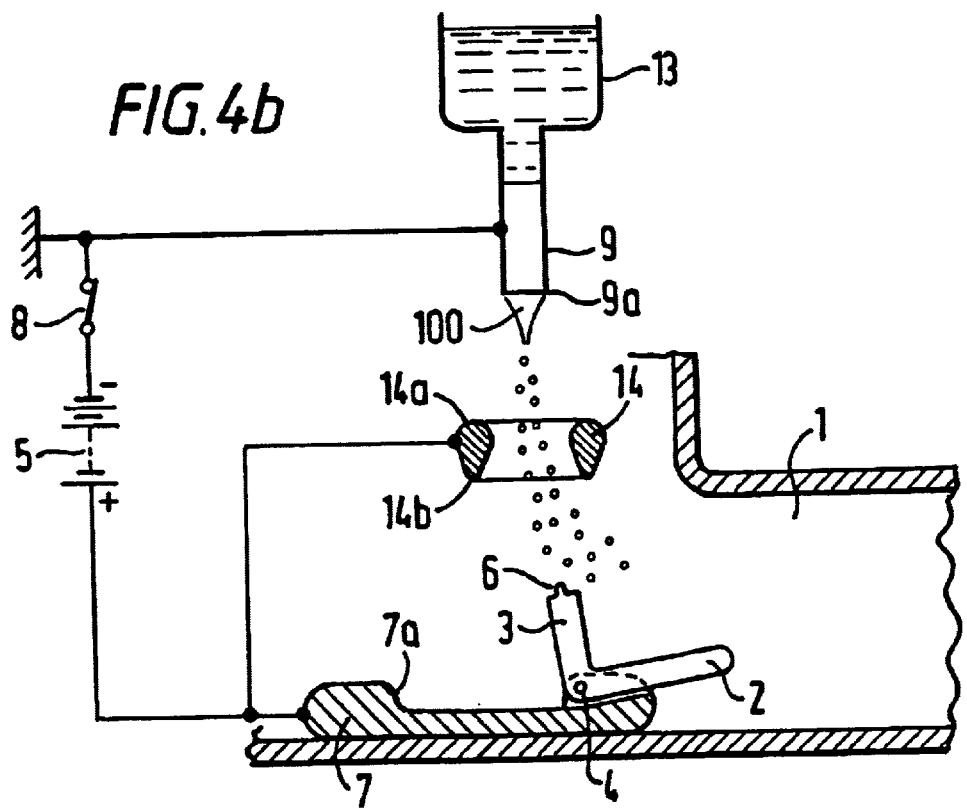

An alternative method of creating the required induction potential to atomize the liquid and subsequently discharge the droplets before impingement upon the induction electrode is to use an induction electrode (14) such as, for example, a ring with two distinct cross-sectional radii of curvature, as shown in FIG. 4. This method may be used with or without a flap valve (2), or field modifying capacitor (s) (11). The larger radius faces toward the nozzle tip, whilst the smaller radius (say less than about 1.0 mm) faces away from the nozzle (9). It has been found that, by very careful design of the field pattern, charged droplets may have sufficient inertial force to pass through a gap in the electrode (14) without immediate impingement. Although these droplets are then almost immediately forced back to impinge upon the electrode, they may be prevented from doing so by the neutralizing action of the fast moving gaseous ions. It has been further discovered that production of gaseous ions by gas breakdown at the smaller radius of curvature may be delayed by maintaining the field strength at the electrode below the critical value until the charged droplets enter the field, whereupon they will increase the field strength to the critical value and immediately trigger the droplet discharge process.

The critical field strength and shape is a function of: electrode position, shape, and voltage; the relative positions and potentials of the nozzle and capacitor(s) surfaces and the degree and position of space charge potential created by the charged droplets.

It has also been found that the methods of controlled field modification (with time) disclosed herein may be so set as to both discharge and, if required, to recharge the droplets to an optimal value. This could be importance in, say, ensuring accurate deposition of droplets within a human lung, where both the droplet's mass, and its charge have controlling influence upon the zones of deposition within the system of airways through which the droplets pass during inhalation.

Figure 5:
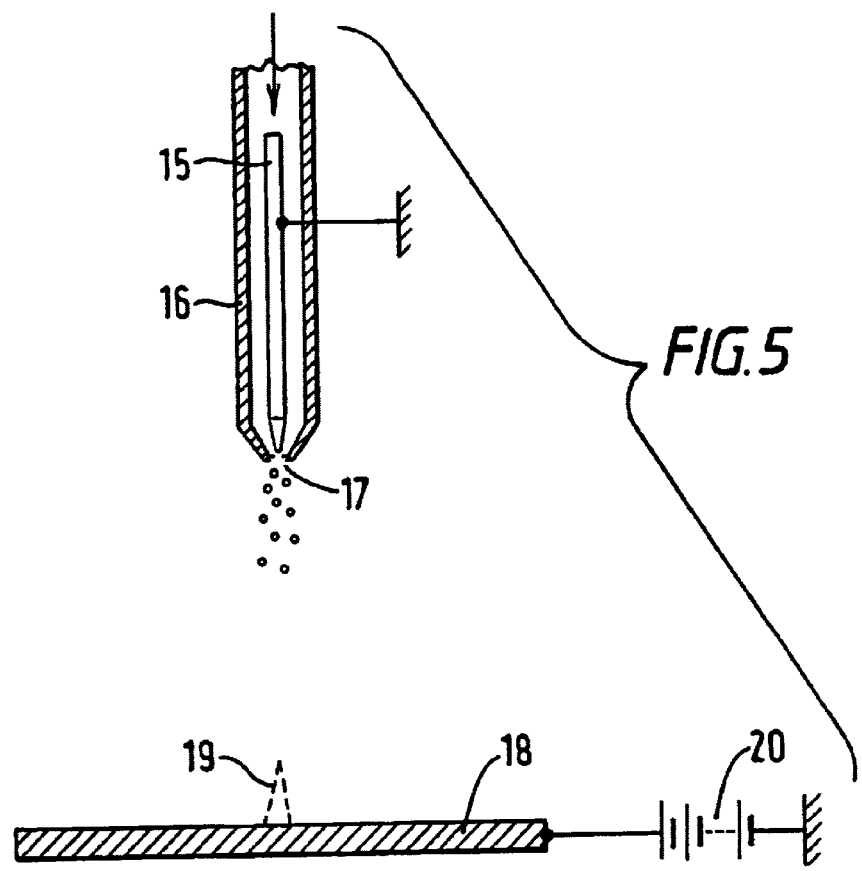
FIG. 5 illustrates a device which uses a controlled field modification technique to both discharge and recharge droplets to an optimal value.

A particular example of the device and its operation is shown in FIG. 5: An earthed needle, (15) concentrically located within a non-conducting sleeve (16) allowed liquid to flow (by gravity or other light pressure) to an outlet nozzle (17) where the liquid was exposed to a strong convergent electric field provided by a high potential supplied to the flat, smooth surface of electrode (18). This resulted in an induced electrohydrodynamic (EHD) communition of the liquid emerging from capillary nozzle (17).

After the communition was established (and within less than one second) a sharp element (19) of the induction electrode (18) was exposed.

The exposure of (19) above the smooth surface of (18) produced gaseous ions of the polarity of the high voltage dc, generator (20). Since the EHD spray cloud was induced from an earthed electrode-nozzle (17), the gaseous ions and the spray droplets have opposing polarities. And as the gaseous ions have much greater mobility in the electric field containing both droplets and ions, the droplets were bombarded and hence electrically discharged.

In the experiment described, the distance between tip of nozzle (17) and flat electrode was 30 mm. When the sharp electrode (19) was positioned to discharge the droplets, the distance between tip of nozzle (17) and needle-tip (19) was 23 mm. The liquid flow-rate was 1.34 µl/sec. The high voltage source was set at a negative potential of 10.7 kilovolts.

The liquid used was 80% ethanol and 20% polyethylene glycol (200), having a viscosity of 2.2 c Poise, a surface tension of 25.0 m N/m, a resistivity of $1.7 \times 10^3$ ohm.m and a density of 0.86 kg/liter.

The discharging effect was assessed to be essentially 100 per cent.

What is claimed is:

1. An inhaler for enabling inhaled administration to and via the nasal mucosa, the inhaler comprising a housing having an outlet duct providing an air passageway through which a user can inhale, the housing containing:
    a liquid container having a liquid outlet; and
    means for applying a high voltage to cause liquid issuing from the liquid outlet to emerge as a jet which breaks up into charged droplets which are caused, by the act of the user inhaling, to flow towards the outlet duct.

2. An inhaler for enabling inhaled administration to and via the nasal mucosa, the inhaler comprising a housing having an outlet providing an air passageway through which a user can inhale, the housing containing:
    a liquid container having a liquid outlet; and
    an applicator of a high voltage to cause liquid issuing from the liquid outlet to emerge as a jet which breaks up into charged droplets which are caused, by the act of the user inhaling, to flow towards the outlet duct.

3. An inhaler for enabling inhaled administration, the inhaler comprising a housing having an outlet duct defining a passageway through which air can be drawn by inhalation on the part of a user, the housing containing:
    a capillary nozzle;
    a container for containing a quantity of liquid to be supplied to the capillary nozzle; and
    a voltage producer for producing a voltage in the liquid prior to issue from the container via the capillary nozzle to expose the liquid to an electric field to cause comminution of the liquid emerging from the capillary nozzle to produce a spray of electrically charged droplets, where, when a user inhales via the outlet duct, electrically charged droplets are supplied via the outlet duct for deposition in the user's airways.

4. An inhaler for enabling inhaled administration of a medicament to and via the nasal mucosa, the inhaler having a housing having an outlet duct defining a passageway through which air can be drawn by inhalation by a user, the housing containing:
    a liquid container containing a quantity of liquid and having an outlet; and
    a voltage applier for applying a voltage to the liquid before it emerges from the outlet to subject the liquid to an electric field to cause comminution of liquid emerging from the outlet to produce a spray of electrically charged droplets, wherein, when a user inhales via the outlet duct, electrically charged droplets are supplied via the outlet duct and into the user's airways.

5. An inhaler for enabling inhaled administration of a medicament to and via the lower respiratory tract, the inhaler having a housing having an outlet duct defining a passageway through which air can be drawn by inhalation by a user, the housing containing:
    a liquid container containing a quantity of liquid and having an outlet; and
    a voltage applier for applying a voltage to the liquid before it emerges from the outlet to subject the liquid to an electric field to cause comminution of liquid emerging from the outlet to produce a spray of electrically charged droplets, wherein, when a user inhales via the outlet duct, electrically charged droplets are supplied via the outlet duct and into the user's airways.

6. An inhaler for enabling inhaled administration to and via the nasal mucosa, the inhaler comprising a housing having an outlet duct providing an air passageway through which a user can inhale, the housing containing:

a liquid supplied for containing a quantity of liquid, the liquid supplier having a non-conductive sleeve with an outlet and also having a needle located within the sleeve; and an electric field generator for generating an electric field at the sleeve outlet to cause liquid issuing from the sleeve outlet to emerge as a jet which breaks up into charged droplets for supply, in response to the user inhaling, to and via the nasal mucosa, the electric field generator including a voltage applier for applying a voltage to the liquid prior to issue from the outlet.

7. An inhaler for enabling inhaled administration to and via the nasal mucosa, the inhaler comprising a housing having an outlet duct providing an air passageway through which a user can inhale, the housing containing:

a liquid supplier for containing a quantity of liquid, the liquid supplier having an outlet; and an induction charged adapted to induce a voltage at the liquid supplier outlet to cause liquid issuing from the outlet to emerge as a jet which breaks up into charged droplets for supply to a zone of deposition within the user's airways when air is drawn through the passageway by inhalation by the user.

8. An inhaler for enabling inhaled administration to and via the nasal mucosa, the inhaler comprising a housing having an outlet duct providing an air passageway through which a user can inhale, the housing containing:

a liquid supplier for containing a quantity of liquid, the liquid supplier having an outlet; and a syringe pump for causing liquid to be pumped to the liquid supplier outlet; and a voltage applier for applying a voltage to the liquid prior to issue from the liquid supplier outlet so as to subject the liquid to an electric field to cause comminution of liquid emerging from the outlet to produce a spray of electrically charged droplets to be supplied to a zone of deposition within the user's airways when air is drawn through the passageway by inhalation by the user.

* * * * *